US012653798B2

(12) United States Patent
Muñoz Martínez et al.

(10) Patent No.: US 12,653,798 B2
(45) Date of Patent: Jun. 16, 2026

(54) FIXED COMBINATION MEDICINE FOR THE CONTROL AND MANAGEMENT OF NEUROPATHIC PAIN

(71) Applicant: LABORATORIOS SILANES S.A. DE C.V., Mexico City (MX)

(72) Inventors: Cecilia Jannette Muñoz Martínez, Mexico City (MX); Jorge Alejandro González Canudas, Mexico City (MX); Paola Yazmín Ollervides Rubio, Mexico City (MX); Sixto Serafín Espinoza León, Mexico City (MX); Claudia Delfina Farfán Salazar, Mexico City (MX)

(73) Assignee: LABORATORIOS SILANES S.A. DE C.V., Mexico City (MX)

( * ) Notice: Subject to any disclaimer, the term of this patent is extended or adjusted under 35 U.S.C. 154(b) by 476 days.

(21) Appl. No.: 18/255,229

(22) PCT Filed: Dec. 4, 2020

(86) PCT No.: PCT/MX2020/050049
§ 371 (c)(1),
(2) Date: May 31, 2023

(87) PCT Pub. No.: WO2022/119429
PCT Pub. Date: Jun. 9, 2022

(65) Prior Publication Data
US 2023/0414545 A1 Dec. 28, 2023

(51) Int. Cl.
*A61K 31/192* (2006.01)
*A61K 9/48* (2006.01)
(Continued)

(52) U.S. Cl.
CPC .............. *A61K 31/192* (2013.01); *A61K 9/48* (2013.01); *A61K 31/4415* (2013.01); *A61K 31/51* (2013.01); *A61K 31/714* (2013.01)

(58) Field of Classification Search
CPC .............. A61K 2300/00; A61K 31/192; A61K 31/4415; A61K 31/51; A61K 31/714; A61K 45/06; A61K 9/48; A61P 29/00
See application file for complete search history.

(56) References Cited

U.S. PATENT DOCUMENTS

2011/0059171 A1 3/2011 Senosiain Aguilar et al.

FOREIGN PATENT DOCUMENTS

CA 2717900 C 5/2016
EP 2255803 A1 12/2010
(Continued)

OTHER PUBLICATIONS

Francesc Cabré, PhD et al., Analgesic, Antiinflammatory, and Antipyretic Effects of S(+)-Ketoprofen In Vivo, Journal of Clinical Pharmacology, 1998; pp. 3S-10S, vol. 38, The American College of Clinical Pharmacology, Spain.
(Continued)

*Primary Examiner* — Savitha M Rao
(74) *Attorney, Agent, or Firm* — Hudak, Shunk & Farine Co. LPA

(57) ABSTRACT

The manufacture of fixed-dose combination drug products to be used as an anti-inflammatory and antineuritic agents for the control and management of pain, particularly moderate to severe intensity acute pain of different etiologies resulting from peripheral neuropathies, low back pain, sciatica, neck pain, radiculitis, post-herpetic neuralgia, spondylitis, carpal tunnel syndrome, fibromyalgia, etc., of different etiologies such as inflammatory, drug, diabetic, alcoholic, or nutritional etiology, etc. These fixed-dose combination drug
(Continued)

products contain a therapeutically effective amount of (a) a non-steroidal anti-inflammatory drug (NSAID) or a pharmaceutically acceptable salt thereof, (b) an antineuritic agent or a pharmaceutically acceptable salt thereof, and (c) at least one pharmaceutically acceptable amount of a pharmaceutically acceptable excipient.

14 Claims, 2 Drawing Sheets

(51) Int. Cl.
| | | |
|---|---|---|
| A61K 31/4415 | (2006.01) | |
| A61K 31/51 | (2006.01) | |
| A61K 31/714 | (2006.01) | |

(56) References Cited

FOREIGN PATENT DOCUMENTS

| | | | | |
|---|---|---|---|---|
| MX | 282576 | 1/2011 | | |
| MX | 293045 | 12/2011 | | |
| MX | 346273 | 2/2017 | | |
| WO | 2009109836 A1 | 9/2009 | | |
| WO | WO-2013095315 A1 * | 6/2013 | .......... | A61K 9/0007 |
| WO | 2014098552 A1 | 6/2014 | | |

OTHER PUBLICATIONS

M. Cristina Castelli et al., Pharmacokinetics of Oral Cyanocobalamin Formulated With Sodium N-[8-(2-hydroxybenzoyl)amino]caprylate (SNAC): An Open-Label, Randomized, Single-Dose, Parallel-Group Study in Healthy Male Subjects, Clinical Therapeutics, May 24, 2011, pp. 934-945, vol. 33, No. 7, Elsevier HS Journals, Inc.

Fernanda Martins Gazoni et al., B Complex Vitamins for analgesic therapy, Review Article, 2016, pp. 52-56, vol. 17, Issue No. 1, Sociedade Brasileira para o Estudo da Dor.

Jorge González-Canudas et al., Bioequivalence evaluation of two oral formulations of Dexketoprofen-trometamol (solution and tablets) in healthy subjects: Results from a randomized, single-blind, crossover study, Trends in Medicine, 2019, pp. 1-5, vol. 19, Open Access Text.

Manfaluthy Hakim et al., Management of peripheral neuropathy symptoms with a fixed dose combination of high-dose vitamin B1, B6 and B12: A 12-week prospective non-interventional study in Indonesia, Asian Journal of Medical Sciences, Jan. 1, 2018, pp. 32-40, vol. 9, Issue 1, Asian Journal of Medical Sciences.

Bhavani Jayabalan et al., Vitamin B supplementation for diabetic peripheral neuropathy, Singapore Med J, 2016, pp. 55-59, vol. 57, Issue 2, Singapore.

Esther Jiménez Martínez et al., Estudio de la eficacia analgésica del Dexketoprofeno Trometamol 25 mg. vs. Ibuprofeno 600 mg. tras su administración oral en pacientes sometidos a una intervención quirúrgica oral, Cirugía Bucal / Oral Surgery, Apr. 21, 2003, pp. 138-148.

Levin, et al., The Influence of Pyridoxine in Diabetic Peripheral Neuropathy, Diabetes Care, 1981, pp. 606-609, vol. 4, Issue No. 6.

G. Letizia Mauro, et al., Vitamin B12 in low back pain: a randomised, double-blind, placebo-controlled study, European Review for Medical and Pharmacological Sciences, 2000, pp. 53-58, vol. 4, Italy.

Juan Sánchez-Carpena et al., Comparison of intravenous dexketoprofen and dipyrone in acute renal colic, Eur J Clin Pharmacol, 2007, pp. 751-760, vol. 63, Springer-Verlag.

Yu Sun et al., Effectiveness of Vitamin B12 on Diabetic Neuropathy: Systematic Review of Clinical Controlled Trials, Acta Neurologica Taiwanica, Jun. 2, 2005, pp. 48-54, vol. 14, No. 2.

M.A. Mibielli et al., Diclofenac plus B vitamins versus diclofenac monotherapy in lumbago: the DOLOR study, Current Medical Research and Opinion, 2009, pp. 2589-2599, vol. 25, Issue No. 11, Taylor & Francis.

Neuro Tazarol®, Jul. 30, 2021.

Héctor A. Ponce-Monter et al., Effect of Diclofenac with B Vitamins on the Treatment of Acute Pain Originated by Lower-Limb Fracture and Surgery, Pain Research and Treatment, 2012, pp. 1-5, vol. 2012, Article ID 104782, Hindawi Publishing Corporation.

* cited by examiner

FIXED COMBINATION MEDICINE FOR THE CONTROL AND MANAGEMENT OF NEUROPATHIC PAIN

FIELD OF THE INVENTION

This invention belongs to the healthcare industry, specifically to the pharmaceutical industry, and it is related to the manufacture of combination drug products for the control and management of neuropathic pain.

BACKGROUND OF THE INVENTION

There are studies on the potential use of vitamin B complex to treat different types of pain and neuropathies (Levin, E. R. 1981; Mauro, G. L., 2000; Hakim, M., 2018; Jayabalan, B., 2016; Suy Y., 2005; Gazoni, F. M., 2016). Likewise, other studies on the pain-killing capacity of the B vitamins thiamine, pyridoxine, and cyanocobalamin (B1, B6, B12) have been described, and they suggest the clinical usefulness that the Vitamin B Complex may play in the treatment of neuropathic pain following an injury, an inflammatory process, and degeneration, or in other nervous system disorders in humans (Wang, Z-B., 2005). There are other studies on the pharmacokinetics of oral cyanocobalamin formulated with sodium N-[8-(2-hydroxybenzoyl) amino]caprylate (SNAC), such as the open-label, randomized, single-dose, parallel-group study carried out in healthy male subjects (Castelli, M. C.; 2011), comparing the pharmacokinetics and tolerance of 2 cyanocobalamin formulations: an oral immediate-release formulation and a formulation enhanced with an N-[8-(2-hydroxybenzoyl) amino] caprylate (SNAC) transporter. This study found that, when compared to the other groups, the SNAC formulation improved cobalamin absorption in addition to decreasing $T_{max}$. Both the oral and the parenteral formulations showed a good safety profile, as they were well tolerated by the volunteers.

On the other hand, the pain-killing efficacy of dexketoprofen trometamol when compared to other analgesics such as ibuprofen, dipyrone, diclofenac, and indomethacin is well-known (Sanchez-Carpena, J., 2007; Jiménez Martínez, E., 2004; Cabré F., 1998). For instance, Table 1 shows a comparison of the pharmacokinetic parameters of dexketoprofen vs. those of other NSAIDs. Other studies have compared the bioequivalence of oral formulations of dexketoprofen trometamol solutions and tablets with that of reference drugs (González-Canudas J; 2019); the data of these studies show that, while the solution formulation has an earlier and higher maximum exposure (C) than that of the tablet formulation, the total exposure of both formulations is equivalent ($AUC_{0-t}$ and $AUC_{0-\infty}$). This could suggest an early onset of the pain-killing effect which, in addition to the advantage of the administration without water and the access- and use-facilitating sachets dosage form, represents an interesting option for the treatment of acute pain.

The clinical study comparing the efficacy of 75 mg diclofenac and a combination of 75 mg diclofenac with B vitamins (1 mg cyanocobalamin, 100 mg thiamine, and 100 mg pyridoxine) is presented in the article "Effect of Diclofenac with B Vitamins on the Treatment of Acute Pain Originated by Lower-Limb Fracture and Surgery" of the scientific literature. The evaluations showed a significant decrease when compared to the reference values. However, the combination of diclofenac and B vitamins was more effective in reducing pain than diclofenac alone. The study showed that, when diclofenac and B vitamins were combined, the pain-killing effect increased (https://www.uaeh.edu.mx/investigacion/productos/5660/artfernandezbr3-2012 pdf).

The purpose of the patent "Pharmaceutical Composition comprising the combination of a non-steroidal anti-inflammatory drug, an adjuvant agent, and an antineuritic analgesic, having an antinociceptive effect", document MX 346273, is to offer a pharmaceutical composition made of the synergistic combination of a non-steroidal anti-inflammatory drug (Meloxicam), an adjuvant agent (Melatonin), and an antineuritic analgesic (B-complex vitamins), which are formulated in a single dosage unit indicated for the treatment of pain of different etiologies, for instance, inflammatory originated pain, low back neuropathy, diabetic neuropathy, trigeminal neuralgia, and sciatic neuralgia.

The patent "Oral galenic formulation including ketorolac and B-complex vitamins, in which Vitamin B6 is in an outer layer separated from the rest of the active principles" bearing the patent code WO 2009/109836 A1 describes the solid oral pharmaceutical combination of ketorolac and a vitamin B complex consisting, among others, of Thiamine, pyridoxine, and Cyanocobalamin (Vitamins B1, B6, and B12, respectively) and/or their pharmaceutically acceptable salts, additional pharmaceutically acceptable vehicles and/or excipients; the manufacturing process and the use of said composition with synergistic therapeutic activity indicated for the treatment of moderate to severe pain or neuralgia of different locations is also described in this patent.

In its main claim, the Mexican patent MX 282576 protects a pharmaceutical composition for the oral administration of tablets characterized by the inclusion of a first compartment containing therapeutically effective amounts of ketorolac, vitamin B1, vitamin B12, or their pharmaceutically acceptable salts, a compressible vehicle, a binder, a diluent, an antistatic agent, a lubricant, a plasticizer, and a disintegrant; a second compartment made of an insulating shell or layer containing a coating polymer; and a third compartment containing pyridoxine or its pharmaceutically acceptable salts and a polymer binder.

In its main claim, the Mexican patent MX 293045 protects a pharmaceutical formulation for a solid solution, suspension, or emulsion characterized by the inclusion of a)

TABLE 1

| | Pharmacokinetic parameters of different NSAIDs Nonsteroidal anti-inflammatory agent (NSAIDs) | | | | |
|---|---|---|---|---|---|
| Molecule | Bioavailability (%) | $t_{max}$ (h) | $C_{max}$ (mg/L) | AUC, ($\mu \cdot$ h/mL) | $t_{1/2}$ (h) |
| Dexketoprofen trometamol | 84.5 | 0.5-1.0 | 3.2 | 4.53 ± 0.88 | 1.2-2.5 |
| Ketorolac | 80 | 0.33-1.0 | 5.42 | 4.81 | 3.0-6.0 |
| Meloxicam | 89 | 3.0-6.0 | 1.62 ± 0.20 | 28.8 | 20-25 |
| Diclofenac | 50-60 | 1.98 | 0.1-2.2 | 4.4 ± 0.08 | 1.0-2.0 |
| Ibuprofen | 80 | 2 | 20 | 70 | 2 | meloxicam, b) cyanocobalamin, c) pyridoxine, d) thiamine, in addition to pharmaceutically acceptable excipients formulated in a single dosage unit.

It also claims the use of the pharmaceutical formulation to manufacturing a drug product to treat low back pain, neck pain, brachialgia, radiculitis, and peripheral neuropathies with different etiopathogenesis, such as trigeminal neuralgia, trigeminal neuralgia, alcoholic neuropathy, diabetic neuropathy, fibromyalgia, muscle strains, and pain and inflammation in soft tissues and respiratory tracts caused by different etiologies.

However, considering the dexketoprofen trometamol pain-killing efficacy when compared to other analgesics, no fixed-dose oral dosage form for the dexketoprofen-B complex combination has been described or exists in the market; therefore, there is no scientific evidence supporting this combination, its advantages, or stability when administered in a single dose and formulated in a single-immediate-release dosage form to be used as a useful drug product with anti-inflammatory and antineuritic properties or to control and manage pain.

SUMMARY OF THE INVENTION

This invention is a fixed-dose combination drug product intended to be used as an anti-inflammatory and an antineuritic agent for the control and management of pain, particularly of moderate- to severe-intensity acute pain of different etiologies resulting from peripheral neuropathies, low back pain, sciatica, neck pain, radiculitis, post-herpetic neuralgia, spondylitis, carpal tunnel syndrome, fibromyalgia, etc., of different etiologies such as inflammatory, drug, diabetic, alcoholic, or nutritional etiology, etc. This fixed-dose combination drug product contains a therapeutically effective amount of (a) a non-steroidal anti-inflammatory drug (NSAID) or a pharmaceutically acceptable salt thereof; (b) an antineuritic agent or a pharmaceutically acceptable salt thereof; and (c) at least one pharmaceutically acceptable amount of a pharmaceutically acceptable excipient.

The non-steroidal anti-inflammatory drug (NSAID) is dexketoprofen trometamol or a pharmaceutically acceptable salt thereof, and the antineuritic agent is a combination of B complex vitamins or pharmaceutically acceptable salts thereof.

In one of the forms of the invention, the B complex contains at least one of the following substances: vitamin B12 (cyanocobalamin), vitamin B1 (thiamine), vitamin B6 (pyridoxine), or it is a combination of any of these vitamins, or their pharmaceutically acceptable salts. Vitamin B1 is preferably present as thiamine, mononitrate; and vitamin B6 is preferably present as pyridoxine hydrochloride.

In another part of the invention, at least one pharmaceutically acceptable excipient is selected from the group of diluents, binders, disintegrants, emulsifiers or solubilizers, adsorbents, and lubricants, or a combination thereof.

In one of the forms of the invention, the diluent is preferably a pharmaceutically acceptable amount of corn starch within the 3.0-10% range; the binder is a pharmaceutically acceptable amount of polyethylene glycol 6000 within the 10-15% range; the disintegrant is a pharmaceutically acceptable amount of crospovidone within the 2.0-5.0% range; the solubilizer is a pharmaceutically acceptable amount of poloxamer 188 within the 5.0-10.0% range; the adsorbent is a pharmaceutically acceptable amount of magnesium aluminum silicate within the 0.5-90% range; and the lubricant is a pharmaceutically acceptable amount of magnesium stearate within the 0.25-5.0% range.

One of the preferred forms of the invention is the fixed-dose combination drug product ideally containing a combination of dexketoprofen trometamol, cyanocobalamin, thiamine mononitrate, and pyridoxine hydrochloride in addition to pharmaceutically acceptable excipients; in this form, the therapeutically effective amount of dexketoprofen trometamol is 12.5 to 75 mg/day, ideally, 36.91 mg (equiv to 25 mg), and the therapeutically effective amounts of vitamin B12 (cyanocobalamin), vitamin B1 (thiamine, mononitrate), and vitamin B6 (pyridoxine, hydrochloride) are 0.50, 100.00, and 50.00 mg respectively.

Another part of the invention describes the manufacturing method of the combination drug product, which is presented in a solid dosage form to be orally administered; this dosage form is stable and immediately released. The solid dosage form is a solid dosage unit that is selected from the group consisting of tablets, pellets, caplets, granules, lozenges, pills, and capsules; capsules are the preferred form.

The manufacture of the combination drug product includes the selection of unit operations as per their execution order and time to control the different physicochemical properties of the drugs. Said operations include heating, granulating, cooling, mixing, and sieving processes.

One additional form describes the use of the fixed-dose combination drug product to control and manage pain. Pain here is described as moderate to severe intensity acute pain of different etiologies. For example, the form describes the use of a therapeutically effective amount of (a) a non-steroidal anti-inflammatory drug (NSAID) such as dexketoprofen trometamol, or a pharmaceutically acceptable salt thereof; (b) an antineuritic agent such as a combination of the vitamins contained in the B complex/group as described above or a pharmaceutically acceptable salt thereof; and (c) at least one pharmaceutically acceptable excipient for the manufacture of a fixed-dose combination drug product useful as an anti-inflammatory or antineuritic agent and in the control and management of pain in an individual suffering from pain.

An additional part of the invention explains that the fixed-dose combination drug product shows more efficacy in the control and management of pain experienced by an individual.

DETAILED DESCRIPTION OF THE INVENTION

Definitions

Figure 1:
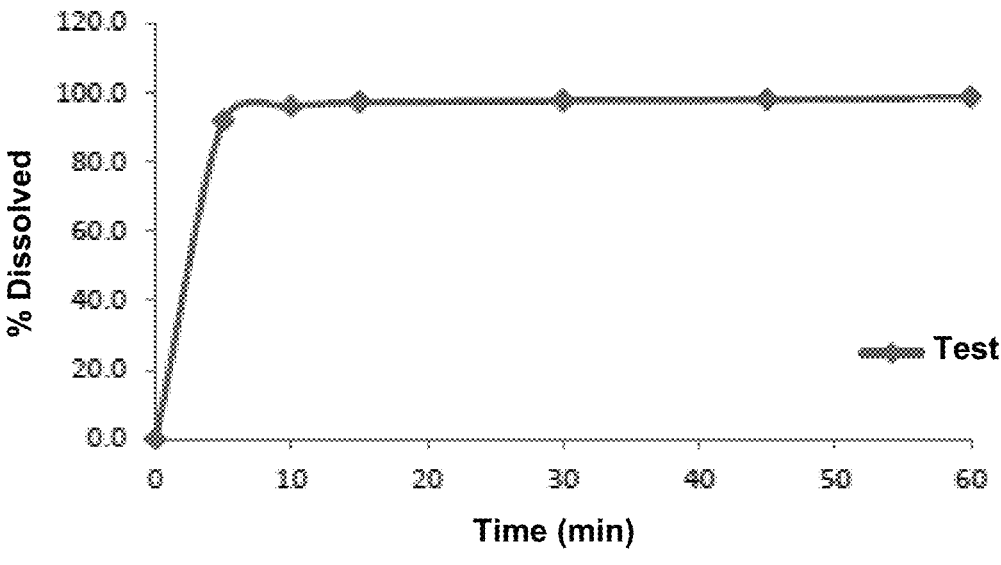
FIG. 1. Dissolution profile of pyridoxine hydrochloride
FIG. 2. Dissolution profile of thiamine mononitrate
FIG. 3. Dissolution profile of dexketoprofen trometamol
FIG. 4. Average time flows in an arithmetic scale for both study periods following the plasma concentration of dexketoprofen up to the 14-hours-sample
Figure 2:
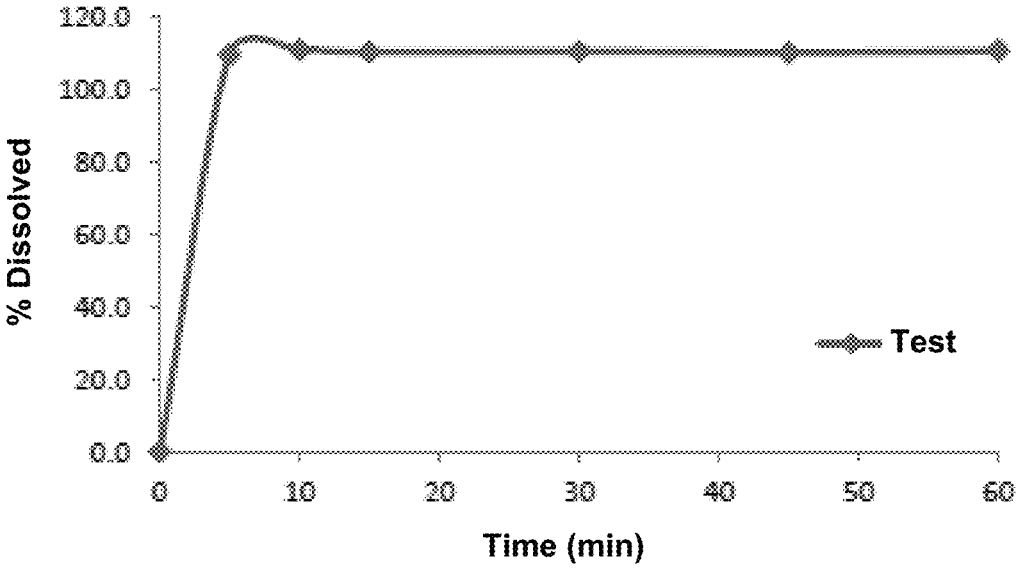
Figure 3:
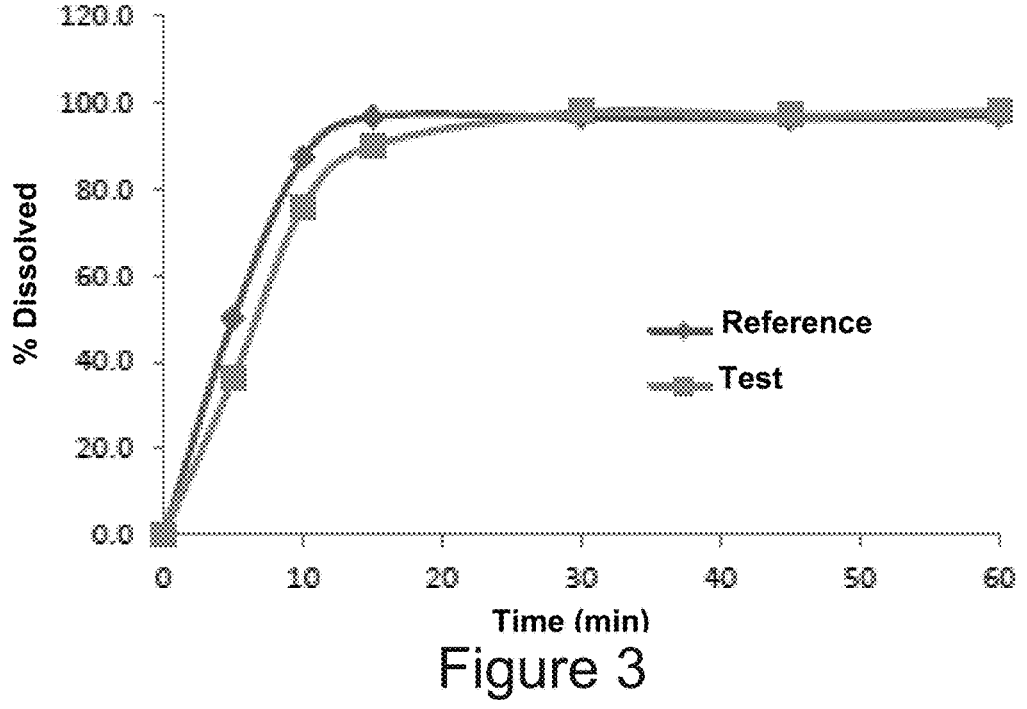

Pharmaceutically acceptable salt. For the purposes of this invention, the term "pharmaceutically acceptable salt" refers to a compound that maintains biological efficacy and properties that are not biologically, or otherwise, undesirable (P. Heinrich Stahl and Camille G. Wermuth (Eds.). Pharmaceutical Salts Properties, Selection, and Use (International Union of Pure and Applied Chemistry), Wiley-VCH; $2^a$ Revised Edition (May 16, 2011)). Pharmaceutically acceptable base addition salts can be prepared from inorganic or organic bases. Some examples of salts deriving from inorganic bases include sodium, potassium, lithium, ammonium, calcium, and magnesium salts. Some examples of salts deriving from organic bases include primary, secondary, and tertiary amine salts. Specific examples of adequate amines include isopropylamine, trimethylamine, diethylamine, tri (isopropyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and similar.

Pharmaceutically acceptable base addition salts can be prepared from inorganic or organic acids. Salts deriving from inorganic acids include hydrochloric acid, hydrobromic acid, sulfuric acid, nitric acid, phosphoric acid, and similar. Salts deriving from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and similar.

Excipient. For the purposes of this invention, the word "excipient" refers to the ingredients that are part of this pharmaceutical composition including, among others, diluents, disintegrants, lubricants, coating agents, and absorbents.

Stability. It is the ability that a pharmaceutical product has to maintain its chemical, physical, microbiological, and pharmaceutical properties within the specified limits throughout its shelf life.

This invention is a stable innovative drug product that is adapted to be immediately released through a single dosage unit, and it is intended to be used as an anti-inflammatory and an antineuritic agent to treat, better control, and manage the pain of an individual, while also solving a set of major technological challenges encountered in its manufacture as a result of the physicochemical properties and dose differences of the combination of the drug substances contained in it to secure the obtaining of a product that is stable and fulfills the aforementioned purposes. Therefore, a fixed-dose combination drug product is described as a product that contains a therapeutically effective quantity of (a) a non-steroidal anti-inflammatory drug (NSAID) or a pharmaceutically acceptable salt thereof; (b) an antineuritic agent or a pharmaceutically acceptable salt thereof; and (c) at least one pharmaceutically acceptable amount of a pharmaceutically acceptable excipient. Likewise, this drug product is presented in a solid, stable, and immediate-release dosage form.

The reduction of the adverse effects of this anti-inflammatory drug is the result of the decrease of the dose used in the B complex combined with other drugs, such as 100 mg diclofenac and 100 mg metamizole; in some cases, this reduction is the result of the fewer adverse effects observed in these drugs when compared to the lowest dose anti-inflammatory drug and dexketoprofen; this is the case for 10 mg ketorolac and 7.5 mg meloxicam. Likewise, the main difference between dexketoprofen and other NSAIDs is the effect onset ($T_{max}$) and a short half-life, which are advantages for patients with other comorbidities who require additional treatments as, in this case, the risk of drug interactions is reduced (Table 1).

Consequently, the combined therapy with a solid, stable, and immediate-release dosage form to be used in the control and management of pain including, among others, neuropathic pain and acute to severe painful neuropathies, contains dexketoprofen trometamol, which is a non-steroidal anti-inflammatory drug (NSAID) or a pharmaceutically acceptable salt thereof. The antineuritic agent is a combination of B-complex vitamins or pharmaceutically acceptable salts thereof. Ideally, the B complex to be used contains at least one of the following vitamins: vitamin B12 (cyanocobalamin), vitamin B1 (thiamine), vitamin B6 (pyridoxine), or a combination of any of these or their pharmaceutically acceptable salt; in this complex, vitamin B1 occurs as thiamine in its mononitrate form, while vitamin B6 occurs as pyridoxine hydrochloride.

The fixed-dose combination drug product containing an anti-inflammatory and an antineuritic agent used to control and manage pain, specifically moderate- to severe-intensity acute pain of different etiologies that includes the use of a therapeutically effective amount of (a) a non-steroidal anti-inflammatory drug (NSAID) or a pharmaceutically acceptable salt thereof; (b) an antineuritic agent or a pharmaceutically acceptable salt thereof; and (c) at least one pharmaceutically acceptable excipient for the manufacture of a drug product, involves a set of major technological challenges as a result of the physicochemical properties of the drugs. Since the antineuritic agent contains at least one of the following B-complex vitamins: vitamin B12 (cyanocobalamin), vitamin B1 (thiamine), vitamin B6 (pyridoxine); or it is a combination thereof or of their acceptable pharmaceutically acceptable salts, its technological complexity is the result of the existing light sensitivity properties of cyanocobalamin, thiamine, and pyridoxine, as well as of the interaction caused by the presence of humidity. Therefore, achieving stability using a dispersion medium that does not affect the absorption of light and humidity entails the implementation of a water-free process and materials that protect the drugs and do not interfere with their release. On the other hand, the adequate selection of excipients and the manufacturing conditions, as well as the selection of the right doses to ensure the obtaining of a stable product throughout the formulation of the drug product, play a major role in the drugs release and the speed at which the organism absorbs them.

The process is based on the selection of unit operations and the order and time for their execution aiming to control the different physicochemical properties of the drugs; therefore, the critical operations of the manufacturing process are described below:

(a) heating: a heating time of 900 s to 1200 s is necessary to achieve the granulation that protects the drugs with a physical barrier;

(b) granulation: a granulation time or 900 s to 1200 s is necessary to form an uniform granule;

(c) cooling: a minimum cooling time of 1500 s is necessary for easy and adequate handling of the product;

(d) mixing: regarding mixes 2, 3, and 4, a mixing time of 180 s is necessary to achieve uniformity of cyanocobalamin;

(e) sieving: regarding sievings 1, 2, and 3, a sieving speed of 1200 rpm is necessary to homogenize the particle size of drugs and materials in order to achieve uniformity.

A set of tests were carried out. In these tests, the formulation components were selected based on their function, and their concentration was established based on the behavior of the product while ensuring the right performance of the drug product; the absence or alteration of any of these elements implies the noncompliance of the established quality attributes.

The acceptable pharmaceutical excipients and/or vehicles of the pharmaceutical composition regarding this invention include, among others, at least one of the following:

diluents, binders, disintegrants, emulsifiers or solubilizers, adsorbents, and lubricants, or a combination of any of these.

Examples of pharmaceutically acceptable diluents, the function of which is known in the state of the art, include the adjustment and maintenance of the tablet constant weight, as well as the compacting and flow, which include, among others, cellulose derivatives, such as microcrystalline cellulose; phosphate derivatives such as dibasic calcium phosphate; starch derivatives, such as pregelatinized starch and corn starch; as well as mannitol, xylitol, maltitol, lactitol, sorbitol, sucrose, or a combination thereof. In one of the forms, ideally, the diluent is corn starch at a pharmaceutically acceptable quantity within the 3.0-10.0% range, preferably at a 7.5% concentration.

Some examples of pharmaceutically acceptable binders include, among others, hypromellose (various grades), corn starch, cellulose derivatives (hydroxypropyl cellulose, carboxymethylcellulose), hydrogenated vegetable oil derivatives, ethylene glycol derivatives (peg-300, peg-3000), gum derivatives (gum acacia), agar, alginate derivatives (alginic acid), calcium derivatives (calcium carbonate, calcium phosphate), carbomers, chitosan, and povidone derivatives (copovidone, crospovidone, polyvidone). In one of the forms, ideally, the binder is polyethylene glycol 6000, which was selected for this invention, as its melting point is 55-63° C. and makes the use of water to obtain granules unnecessary. It is present in a pharmaceutically acceptable quantity within a 10-15% range, preferably 2.87%.

Pharmaceutically acceptable disintegrants include, among others, croscarmellose, cellulose derivatives such as hydroxypropyl cellulose, carboxymethylcellulose, and microcrystalline cellulose; povidone derivatives such as crospovidone, copovidone; and starch derivatives such as pregelatinized starch, sodium starch glycolate, corn starch, and modified potato starch. In one of the forms, ideally, the disintegrant iscrospovidone, which was selected for this invention due to its high capacity to collect water quickly, increase its volume, and its wetting capacity. This agent offers a shorter disintegration time when compared to other materials and provided it is present in a pharmaceutically acceptable quantity within a 2.0-5.0% range, preferably 4.98%.

Some examples of pharmaceutically acceptable solubilizers include, among others, polyethylene glycol and its derivatives (polyoxetyl alkyl ether, hydrogenated castor oil), sodium lauryl sulfate, sorbitan esters, and benzalkonium chloride. In one of the forms, ideally, the binder is poloxamer 188, which was selected for this invention, as it improves the solubility and stability of the drug substances of the fixed-dose combination drug product; this binder is present in a pharmaceutically acceptable quantity within a 5.0-10.0% range, preferably 2.87%.

The pharmaceutically acceptable adsorbents include, among others, aluminum derivatives (aluminum hydroxide, aluminum oxide, aluminum phosphate), clays or soils (attalpulgite, bentonite, hectorite, kaolin, pectin), silica derivatives (calcium silicate, colloidal silicon dioxide, aluminum, and magnesium silicate), cellulose derivatives (microcrystalline cellulose, cellulose), magnesium derivatives (magnesium carbonate, magnesium silicate), and aluminum and magnesium metasilicate, due to their ability to adsorb residual water in the solid dosage form or water collected through the environment to improve the stability of the drug substances. In one of the forms, ideally, the adsorbent is aluminum and magnesium silicate in a pharmaceutically acceptable quantity within a 0.5 to 90% range, preferably 26.35%.

Examples of pharmaceutically acceptable lubricants include, among others, magnesium stearate, zinc stearate, calcium stearate, stearic acid, monostearate, stearyl fumarate, talc, and sulfated derivatives such as magnesium lauryl sulfate. The lubricant prevents the different tools from sticking to one another during the compression process of the solid dosage form. In one of the forms, ideally, the lubricant is magnesium stearate due to its slip attributes in a pharmaceutically acceptable quantity within a 0.25 to 5.0% range, preferably 0.95%.

On the other hand, the fixed-dose combination drug product is presented in a single solid dosage unit selected from the group consisting of tablets, pellets, caplets, granules, lozenges, pills, and capsules; capsules are the preferred form. The preferred dosage form selected to dose the drug substances was "capsules" due to the accuracy of the dose and because it is a pharmaceutically accepted dosage form, as it is easily administered; tablets are an alternative, however, due to the rheological properties of the powder, carrying out a compression process is more complex.

Once the drug product formulation and process have been evaluated and determined as per the above description, the fixed-dose combination drug product formulation includes the ingredients listed in Table 2.

TABLE 2

| Ingredients of the drug product formulation | |
| --- | --- |
| Components | Function |
| Nonsteroidal anti-inflammatory agent | Drug substance 1 |
| Antineuritic agent | Active ingredients 2, 3, 4, etc. (at least one of the B-complex vitamins, or their combination) |
| Corn starch | Diluent |
| Polyethylene glycol 6000 | Binder |
| Crospovidone | Disintegrant |
| Poloxamer 188 | Solubilizer |
| Magnesium aluminum silicate | Adsorbent |
| Magnesium stearate | Lubricant |
| Capsule No. 0 | Vehicle |

One of the preferred forms of the invention is the fixed-dose combination drug product, which ideally contains a combination of dexketoprofen trometamol, cyanocobalamin, thiamine mononitrate, and pyridoxine hydrochloride in addition to pharmaceutically acceptable excipients; in this form, the therapeutically effective amount of dexketoprofen trometamol is 12.5 to 75 mg/day, ideally, 36.91 mg (equiv to 25 mg), and the therapeutically effective amounts of vitamin B12 (cyanocobalamin), vitamin B1 (thiamine, mononitrate), and vitamin B6 (pyridoxine, hydrochloride) are 0.50, 100.00, and 50.00 mg respectively.

In another form of the invention, the fixed-dose combination drug product availability was determined. A comparison of the bioavailability of dexketoprofen-B complex and dexketoprofen (reference drug) at a dose of 25 mg was carried out in healthy subjects of both genders under fasting conditions to characterize the pharmacokinetic parameters $C_{max}$, AUC, $T_{max}$, Ke, and $T_{1/2}$ of dexketoprofen.

The innovation of the drug product process and formulation allowed obtaining a product with a verified stability in different studies based on current regulations that complied with the quality attributes throughout the evaluation period. Stability tests are a way to compare different formulations, packaging materials, or manufacturing processes in short-lasting experiments. As soon as the final formulation and manufacturing processes are established, the manufacturer performs a group of stability tests allowing to predict the stability of the product or, in this case, the drug product, and determine its shelf life and storage conditions.

Examples 5 and 6 (Tables 8-17) illustrate the initial and accelerated results for the determination of the fixed-dose combination drug product stability of this invention, which is useful in the control and management of pain experienced by an individual under the 40° C./75% RH condition. According to this data, the drug product formulations are dexketoprofen trometamol at a 36.91 mg (equiv to 25 mg) dose, as well as vitamin B12 (cyanocobalamin), vitamin B1 (thiamine, mononitrate), and vitamin B6 (pyridoxine, hydrochloride) at doses of 0.50, 100.00, and 50.00 mg respectively.

The technological development included a series of evaluations in which the formulation and process are outlined as follows. The expert qualified in this technique will find that multiple variations and forms are possible in the execution of this invention without being deviated from its essence and scope to ensure the proper performance of the product and to comply with the required quality attributions.

EXAMPLES

The technological development included a series of evaluations in which the formulation and process are outlined as follows.

Example 1. Qualitative and Quantitative Formula of the Fixed-Dose Combination Drug Product

TABLE 3

| Ingredients of the drug product formulation | | |
|---|---|---|
| mg/capsule | Components | Function |
| 36.91 | Dexketoprofen trometamol | Drug substance 1 |
| 0.50 | Cyanocobalamin | Drug substance 2 |
| 50.00 | Pyridoxine hydrochloride | Drug substance 3 |
| 100.00 | Thiamine mononitrate | Drug substance 4 |
| 40.00 | Corn starch | Diluent |
| 15.00 | Polyethylene glycol 60000 | Binder |
| 26.00 | Crospovidone | Disintegrant |
| 15.00 | Poloxamer 188 | Solubilizer |
| 137.59 | Magnesium aluminum silicate | Adsorbent |
| 5.00 | Magnesium stearate | Lubricant |
| 96.00 | Capsule No. 0 | Vehicle |

Example 2. Manufacturing Process for the Manufacture of the Fixed-Dose Combination Drug Product in the Form of a Capsule Based on the qualitative and quantitative formula detailed in example 1, the unit operations or method for the manufacture of the fixed-dose combination drug product include:
1. Mix the binder, the drug substance 2 (NSAID), the diluent, and 70% of the disintegrant that were previously submitted to a sieving process. Mix the materials for 3 minutes.
2. Start the heating stage to granulate the mixture resulting from step 1.
3. Once the granulation product is obtained, start the cooling stage, which ends upon reaching a 25° C. to 30° C. temperature.
4. Sieve the product obtained in step 3.
5. Mix the drug substance 1 (cyanocobalamin) and 5% of the adsorbing agent for 3 minutes.

6. Mix 11% of the adsorbing agent with the product resulting from step 5 for 3 minutes.
7. Mix 24% of the adsorbent with the product resulting from step 6 for 3 minutes.
8. Mix the product resulting from the sieving stage described in step 4 with the mixture obtained in step 7 for 5 minutes.
9. Sieve the drug substance 3 (pyridoxine, hydrochloride), the drug substance 4 (thiamine, mononitrate), 30% of the disintegrant, the solubilizer, and 60% of the adsorbent.
10. Add the product obtained in the sieving process of step 9 to the mixture obtained in step 8 and mix for 10 minutes.
11. Sieve the lubricant.
12. Add the lubricant to the mixture obtained in step 10 and mix for 5 minutes.
13. Encapsulate following the specifications.

Example 3. Dissolution Profile Tests that Need to be Added

Below are the dissolution profiles of pyridoxine hydrochloride, thiamine mononitrate, and dexketoprofen trometamol.

TABLE 4

| Dissolution of pyridoxine hydrochloride | |
|---|---|
| t (min) | % dissolved |
| 0 | 0.00 |
| 5 | 91.75 |
| 10 | 95.38 |
| 15 | 97.08 |
| 30 | 97.56 |
| 45 | 97.84 |
| 60 | 90.54 |

TABLE 5

| Dissolution of thiamine mononitrate | |
|---|---|
| t (min) | % dissolved |
| 0 | 0.00 |
| 5 | 91.75 |
| 10 | 95.88 |
| 15 | 97.08 |
| 30 | 97.56 |
| 45 | 97.84 |
| 60 | 98.54 |

TABLE 6

| Dissolution of dexketoprofen trometamol | | |
|---|---|---|
| t (min) | Reference | Test |
| 0 | 0.0 | 0.0 |
| 5 | 50.07 | 36.25 |
| 10 | 37.34 | 76.13 |
| 20 | 96.87 | 90.15 |
| 30 | 96.74 | 97.88 |
| 45 | 96.43 | 97.21 |
| 60 | 96.92 | 98.19 |

Example 4. Bioavailability and Pharmacokinetic
Parameters

There is no current description of bioavailability studies in the state of the art regarding the dexketoprofen-B complex (thiamine, pyridoxine, cyanocobalamin) combination. Therefore, there is no described study of non-pharmacokinetic interaction between the drug substances.

This invention of the fixed-dose combination drug product with a therapeutically effective quantity of (a) a non-steroidal anti-inflammatory drug (NSAID) or a pharmaceutically acceptable salt thereof; (b) an antineuritic agent or a pharmaceutically acceptable salt thereof; and (c) at least one pharmaceutically acceptable amount of a pharmaceutically accepted excipient, preferably a combination of dexketoprofen trometamol, cyanocobalamin, thiamine mononitrate and pyridoxine hydrochloride, as well as pharmaceutically acceptable excipients, includes a comparison study on the bioavailability of dexketoprofen-B complex and dexketoprofen (reference drug) at 25 mg dose in healthy subjects of both genders under fasting conditions to characterize the pharmacokinetic parameters $C_{max}$, AUC, $T_{max}$, Ke, and $T_{1/2}$ of dexketoprofen and establish the frequency and type of adverse events observed in both formulations (reference drug A as determined by the health authority and test drug B manufactured by Laboratorios Silanes).

It was a crossover, 2×2, open, prospective, longitudinal, and single-dose study comparing a 25 mg dose of dexketoprofen with a 25 mg dose of dexketoprofen+vitamin B, with two treatments, two periods, two sequences, and a washout period of 7 days. This study was carried out on 36 healthy subjects of both genders under fasting conditions. This study design was proposed based on the provisions of the Agreement determining the type of test to be carried out to demonstrate the interchangeability of generic drugs. According to that list, the type of test to be carried out for the tablets dosage form of the B complex and dexketoprofen is:

B complex, type-A test: dissolution or bioequivalence tests are not required.

Dexketoprofen, type-C test: bioequivalence test.

The results of the study carried out by Mazzei et. al. were taken into consideration to calculate the sample size of this protocol. In said study, the intra-subject variability for dexketoprofen $C_{max}$ was calculated to have an intra-subject % CV value of 0.26. The number of subjects calculated for this protocol was 32, with a power of 0.81; based on the probability of early withdrawal or dropout due to non-compliance with the protocol during the study, a surplus of 4 subjects is included, so the total number of participating subjects was 36.

The drug products, a 25 mg tablet of dexketoprofen or a capsule containing dexketoprofen and vitamin-B complex, were administered orally based on the randomization sequence following a 10-hour fasting period and 4 hours before breakfast with 250 mL of water at room temperature. Afterward, 17 blood samples of approximately 4 mL each were collected at the following times: 0.16, 0.33, 0.5, 0.75, 1, 1.25, 1.5, 2.0, 2.5, 3.0, 4.0, 6.0, 8.0, 10.0, 12.0, 14.0, and 24.0 hours.

All subjects' pharmacokinetic parameters were tabulated indicating the drug product or formulation, the arithmetic mean (X), the standard deviation (SD), the coefficient of variation (CV), the geometric mean, the median, and the minimum and maximum value. Plots of each individual showing the concentration profile regarding time and the plot showing the concentration average±the standard error regarding time were included.

Pursuant to the Mexican standard NOM 177-SSA1-2013, the dexketoprofen plasma concentration profiles for each subject vs. time were plotted. Based on these plots, the following pharmacokinetic parameters were obtained using non-compartmental methods: maximum concentration (Cmax) and the time needed to reach it, (Tmax), and the area under the curve upon the last sampling time (AUCt0), which was calculated using the trapezoidal rule. The elimination rate (ke) constant was calculated using the log-linear regression of the final elimination phase, and the latter was used to calculate the elimination half-life (T½) by dividing 0.693/ke. The area under the curve extrapolated to infinity (AUC∞0) was calculated by adding the coefficient of the last measured concentration between ke; likewise, the mean residence time (MRT) was obtained.

Figure 4:
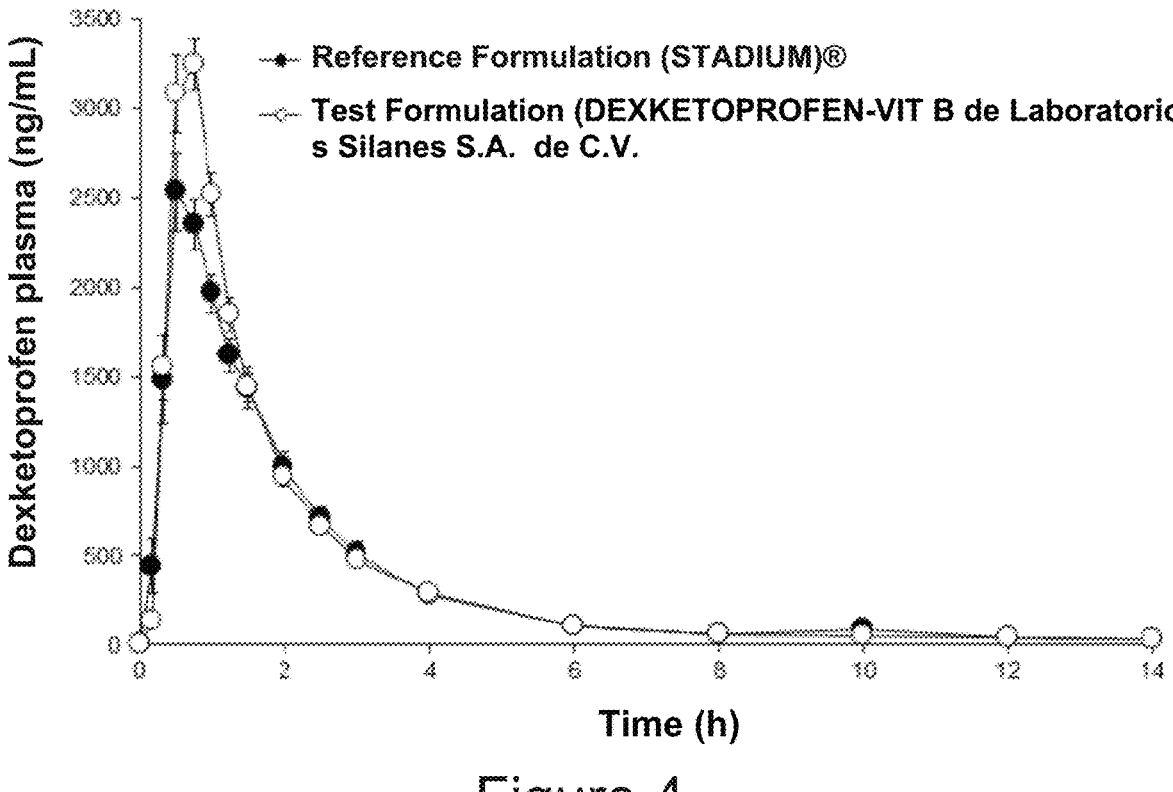

FIG. 4 shows a comparison of the average time courses in an arithmetic scale of both periods of the study for the dexketoprofen plasma concentration until the sample corresponding to 14 h was collected from the subjects who received the reference drug or the test drug.

The individual plots were used to obtain the maximum concentration (Cmax), the time needed to reach this concentration (Tmax), and the area under the curve of the concentrations versus time upon the last sampling point (AUCt0), as well as the AUC extrapolated to infinity (AUC∞0).

The following table shows the descriptive statistics of all dexketoprofen pharmacokinetic parameters for the subjects who received the reference drug or the test drug.

TABLE 7

Descriptive statistics of dexketoprofen pharmacokinetic parameters.

| Pharmacokinetic parameter | Reference formulation | Test formulation |
| --- | --- | --- |
| $C_{max}$ (ng/mL) | 3,254 64 ± 1021.33 | 3,702.21 ± 894 41 |
| $T_{max}$ (h) | 0.89 ± 0.61 | 0.68 ± 0.23 |
| $AUC_{0-t}$ (ng h/mL) | 4,747.32 ± 1084 84 | 5,189.16 ± 1347.41 |
| $AUC_{0-\infty}$ (ng h/mL) | 4,852.21 ± 1091.64 | 5,268.84 ± 1352.78 |
| $T_{1/2}$ (h) | 1.32 ± 0.29 | 1.28 ± 0.23 |

The non-compartmental estimation of the data allowed observing that the average maximum concentration (±SD) of the dexketoprofen-Vitamin B complex product of Laboratorios Silanes, S.A. de C.V. (3,702.21±894.41 ng/mL) was higher than the one produced by the reference drug (3,254.64±1021.33 ng/mL); likewise, said concentration was reached earlier ($T_{max}$: 0.68±0.23 h) when compared to the concentration observed with the reference formulation ($T_{max}$: 0.89±0.61 h). The elimination half-life values were 1.32±0.29 h for the reference drug and 1.28±0.23 h for the dexketoprofen-Vitamin b product of Laboratorios Silanes, S.A. de C.V.

The values of (AUCt0) were 5,189.16±1347.41 ng×h/mL and 4,747.32±1084.84 ng×h/mL; while the values of (AUC∞0) were 5,268.84±1352.78 ng×h/mL and 4,852.21±1091.64 ng×h/mL for the test formulations and the reference formulations, respectively. These results were consistent with the higher values observed in the case of Cmax.

As for the relevant safety and efficacy findings, there were no adverse events observed throughout the clinical study. 35 out of the 36 programmed research subjects completed the study and were discharged with no symptoms showing a general good health status.

Dexketoprofen global exposure as measured by the (AUCt0) and (AUC-0) in the test formulation, dexketoprofen-Vitamin b complex (25 mg capsules) of Laboratorios Silanes, S.A. de C.V., complied with the acceptance criteria of the bioequivalence statistical tests (classical 90% confidence intervals and Schuirmann's Two One-Sided Test) for the reference drug (25 mg tablets).

While the plasma concentration peak ($C_{max}$) was higher for the test product, this difference could have resulted from the fact that the dosage form of the test product (capsule) facilitates the in vivo dissolution process when compared to the dosage form of the reference product (tablet), which was also associated with a lower $T_{max}$ observed with the test drug (0.68±0.23 h) when compared to that of the reference drug (0.89±0.61 h). Either way, the $C_{max}$ of both formulations is within the range previously reported in other studies with similar populations and doses. This could be regarded as a competitive advantage since the maximum benefit is obtained in a shorter time.

No adverse events were observed throughout the study; therefore, the safety profile observed in healthy volunteers was similar across formulations.

Example 5. Drug Product Stability

Analytical Results of the Accelerated Stability (40° C.±2° C./75% RH±5% RH)

Table 8 shows the initial results of the stability determination carried out in the drug product formulations listed below:

TABLE 8

Initial stability data (time zero)

| Determination | Specification | Result Batch 1 |
| --- | --- | --- |
| Cyanocobalamin content | 90-110% | 96.12% |
| Dexketoprofen solution | Q = 70% in 30 min | 94.67% |
| Pyridoxine HCl dissolution | Q = 75% in 45 min | 97.55% |
| Thiamine mononitrate dissolution | Q = 75% in 45 min | 90.17% |

Example 6. Drug Product Stability

Cyanocobalamin Dexketoprofen/Pyridoxine Hydrochloride Thiamine Mononitrate 0.5/25/50/100 mg Capsules
Analytical Results of the Accelerated Stability (40° C.±2° C./75% RH±5% RH)

TABLE 10

Results of the cyanocobalamin content

| Specification | | Initial | 1 month | 3 months | 6 months |
| --- | --- | --- | --- | --- | --- |
| 90.0% | Batch 1 | 118.6% | 111.5% | 112.4% | 111.4% |
| to | Batch 2 | 113.3% | 100.7% | 109.8% | 112.2% |
| 120.0% | Batch 3 | 115.2% | 111.1% | 111.5% | 113.5% |

TABLE 11

Results of the dexketoprofen content

| Specification | | Initial | 1 month | 3 months | 6 months |
| --- | --- | --- | --- | --- | --- |
| 90.0% | Batch 1 | 95.8% | 100.2% | 102.3% | 104.4% |
| to | Batch 2 | 95.8% | 102.2% | 104.9% | 104.3% |
| 110.0% | Batch 3 | 98.8% | 102.0% | 104.8% | 104.4% |

TABLE 12

Results of the pyridoxine hydrochloride content

| Specification | | Initial | 1 month | 3 months | 6 months |
| --- | --- | --- | --- | --- | --- |
| 05.0% | Batch 1 | 98.7% | 106.3% | 106.1% | 100.5% |
| to | Batch 2 | 98.6% | 107.5% | 103.9% | 100.6% |
| 115.0% | Batch 3 | 98.2% | 108.4% | 103.0% | 101.6% |

TABLE 13

Results of the thiamine mononitrate content

| Specification | | Initial | 1 month | 3 months | 6 months |
| --- | --- | --- | --- | --- | --- |
| 00.0% | Batch 1 | 113.1% | 103.5% | 105.2% | 104.6% |
| to | Batch 2 | 113.8% | 103.0% | 104.0% | 102.3% |
| 120.0% | Batch 3 | 112.0% | 103.0% | 105.3% | 103.9% |

TABLE 9

Results of the drug product description

| Specification | | Initial | 1 month | 3 months | 6 months |
| --- | --- | --- | --- | --- | --- |
| Capsule No. 0 with an opaque white body and an opaque brown cap containing beige granules and red dots | Batch 1 | Capsule No. 0 with an opaque white body and an opaque brown cap containing beige granules and red dots | Capsule No. 0 with an opaque white body and an opaque brown cap containing beige granules and red dots | Capsule No. 0 with an opaque white body and an opaque brown cap containing beige granules and red dots | Capsule No. 0 with an opaque white body and an opaque brown cap containing beige granules and red dots |
| | Batch 2 | Capsule No. 0 with an opaque white body and an opaque brown cap containing beige granules and red dots | Capsule No. 0 with an opaque white body and an opaque brown cap containing beige granules and red dots | Capsule No. 0 with an opaque white body and an opaque brown cap containing beige granules and red dots | Capsule No. 0 with an opaque white body and an opaque brown cap containing beige granules and red dots |
| | Batch 3 | Capsule No. 0 with an opaque white body and an opaque brown cap containing beige granules and red dots | Capsule No. 0 with an opaque white body and an opaque brown cap containing beige granules and red dots | Capsule No. 0 with an opaque white body and an opaque brown cap containing beige granules and red dots | Capsule No. 0 with an opaque white body and an opaque brown cap containing beige granules and red dots |

TABLE 14

| Results of the dexketoprofen dissolution | | | | | |
|---|---|---|---|---|---|
| Specification | | Initial | 1 month | 3 months | 6 months |
| Q = 75.0% in | Batch 1 | 92.3% | 95.5% | 98.0% | 93.9% |
| 45 min | Batch 2 | 97.2% | 95.4% | 97.2% | 95.5% |
| | Batch 3 | 98.4% | 97.7% | 95.8% | 98.9% |

TABLE 15

| Results of the pyridoxine hydrochloride dissolution | | | | | |
|---|---|---|---|---|---|
| Specification | | Initial | 1 month | 3 months | 6 months |
| Q = 75.0% in | Batch 1 | 98.2% | 101.6% | 100.2% | 97.5% |
| 45 min | Batch 2 | 99.8% | 99.1% | 99.2% | 90.5% |
| | Batch 3 | 100.7% | 100.4% | 100.0% | 98.2% |

TABLE 16

| Results of the thiamine mononitrate dissolution | | | | | |
|---|---|---|---|---|---|
| Specification | | Initial | 1 month | 3 months | 6 months |
| Q = 75.0% in | Batch 1 | 109.9% | 99.1% | 99.8% | 99.1% |
| 45 min | Batch 2 | 111.8% | 97.6% | 97.8% | 98.4% |
| | Batch 3 | 111.2% | 99.3% | 99.2% | 100.3% |

TABLE 17

| Results of the substances related to dexketoprofen | | | | | |
|---|---|---|---|---|---|
| Specification | | Initial | 1 month | 3 months | 6 months |
| Unknown impurities | Batch 1 | 0.01% | 0.29% | 1.17% | 1.42% |
| Not more than 1.50% | Batch 2 | 0.03% | 0.28% | 1.10% | 1.41% |
| | Batch 3 | 0.03% | 0.13% | 1.04% | 1.41% |
| Ketoprofen related | Batch 1 | Not detected | 0.10% | 0.20% | 0.14% |
| compound D | Batch 2 | Not detected | 0.10% | 0.19% | 0.13% |
| Not more than 1.50% | Batch 3 | Not detected | 0.09% | 0.19% | 0.14% |
| Total impurities | Batch 1 | 0.02% | 0.94% | 3.217% | 4.12% |
| Not more than 5.00% | Batch 2 | 0.05% | 0.91% | 3.12% | 4.04% |
| | Batch 3 | 0.00% | 0.84% | 3.01% | 4.07% |

Implementation and Advantages of the Invention

Currently, no fixed-dose oral dosage form for the dexketoprofen-B complex combination (thiamine, pyridoxine, cyanocobalamin) has been described or exists in the market; therefore, there is no scientific evidence supporting this combination, its advantages, or stability when administered in a single dose and formulated in a single-automatic-release dosage form to be used as a useful drug product to control and manage pain.

The reduction of the adverse effects of this anti-inflammatory drug is the result of the decrease of the dose used in the B complex combined with other drugs, such as 100 mg diclofenac and 100 mg metamizole. In some cases, this reduction is the result of the fewer adverse effects observed in these drugs when compared to the lowest dose anti-inflammatory drug and dexketoprofen; this is the case for 10 mg ketorolac and 7.5 mg meloxicam.

Consequently, this invention is a fixed-dose combination drug product intended to be used as an anti-inflammatory and antineuritic agent for the control and management of pain, particularly moderate- to severe-intensity acute pain of different etiologies resulting from peripheral neuropathies, low back pain, sciatica, neck pain, radiculitis, post-herpetic neuralgia, spondylitis, carpal tunnel syndrome, fibromyalgia, etc., of different etiologies such as inflammatory, drug, diabetic, alcoholic, or nutritional etiology etc. This fixed-dose combination drug product contains a therapeutically effective amount of (a) a non-steroidal anti-inflammatory drug (NSAID) or a pharmaceutically acceptable salt thereof (b) an antineuritic agent or a pharmaceutically acceptable salt thereof, and (c) at least one pharmaceutically acceptable amount of a pharmaceutically acceptable excipient. This drug product is a single-dosage unit combination of the drugs dexketoprofen at a dose of 12.5 to 75 mg/day, preferably 36.91 mg (equiv to 25 mg dexketoprofen); and cyanocobalamin, pyridoxine hydrochloride, and thiamine mononitrate at a dose of 0.5 mg, 50 mg, and 100 mg, respectively; likewise, this product poses a technological challenge due to the properties of the drugs.

REFERENCES

Cabré F, Fernández M F, Calvo L, Ferrer X, Garcia M L, Mauleón D. Analgesic, antiinflammatory, and antipyretic effects of S (+)-ketoprofen in vivo. The Journal of Clinical Pharmacology. 1998; 38(S1):3S-10S.

Castelli M C, Wong D F, Friedman K, Riley M G I. Pharmacokinetics of oral cyanocobalamin formulated with sodium N-[8-(2-hydroxybenzoyl) amino] caprylate (SNAC): an open-label, randomized, single-dose, parallel-group study in healthy male subjects. Clinical therapeutics. 2011; 33(7):934-45.

Gazoni F M, Malezan W R, Santos F C. B complex vitamins for analgesic therapy. Revista Dor. 2016; 17(1):52-6.

González-Canudas J, Garcia-Aguirre L J, Medina-Nolasco A, Ruiz-Olmedo M I, Reyes L J M, Tapia L Z, et al. Bioequivalence evaluation of two oral formulations of Dexketoprofen-trometamol (solution and tablets) in healthy subjects: Results from a randomized, single-blind, crossover study. Trends Med, Vol. 19, pp. 1-5 (2019).

Hakim, M., et al., Management of peripheral neuropathy symptoms with a fixed dose combination of high-dose vitamin B1, B6 and B12: A 12-week prospective non-interventional study in Indonesia. Asian Journal of Medical Sciences, 2018. 9: p. 32.

Jayabalan B, Low L L. Vitamin B supplementation for diabetic peripheral neuropathy. Singapore Medical Journal. 2016; 57(2):55-9.

Jiménez Martínez, E., et al., Study of the analgesic efficacy of Dexketoprofen Trometamol 25 mg. vs. 600 mg ibuprofen following oral administration in patients who underwent oral surgery. Oral Medicine, Oral Pathology, Oral Surgery (printed edition), 2004. 9(2): p. 138-148.

Levin, E. R., et al., The influence of pyridoxine in diabetic peripheral neuropathy. Diabetes Care, 1981. 4(6): p. 606-9.

Mauro, G. L., et al., Vitamin B12 in low back pain: a randomized, double-blind, placebo-controlled study. Eur Rev Med Pharmacol Sci, 2000. 4(3): p. 53-8.

Sanchez-Carpena, J., et al., Comparison of intravenous dexketoprofen and dipyrone in acute renal colic. Eur J Clin Pharmacol, 2007. 63(8): p. 751-60.

Sun Y, Lai M S, Lu C J. Effectiveness of vitamin B12 on diabetic neuropathy: systematic review of clinical controlled trials. Acta Neurol Taiwan. 2005; 14(2):48-54.

Wang Z-B, Gan Q, Rupert R L, Zeng Y-M, Song X-J. Thiamine, pyridoxine, cyanocobalamin and their combination inhibit thermal, but not mechanical hyperalgesia in rats with primary sensory neuron injury. Pain. 2005; 114(1-2):266-77.

What is claimed is:

1. A fixed-dose combination drug product, presented in a solid, stable, and immediate-release dosage form, that comprises:

(a) a therapeutically effective quantity from 12.5 to 75 mg/day of dexketoprofen trometamol as a non-steroidal anti-inflammatory drug (NSAID) or a pharmaceutically acceptable salt thereof;

(b) a therapeutically effective quantity of a combination of B group/complex vitamins or their pharmaceutically accepted salts as an antineuritic agent; and (c) at least one pharmaceutically acceptable amount of a pharmaceutically acceptable excipient selected from the group of: diluents, binders, disintegrants emulsifiers or solubilizers, adsorbents and lubricants or a combination thereof, wherein the diluent is present and is corn starch in the range of 3.0-10% w/w, wherein the adsorbent is present and is aluminum and magnesium silicate in a pharmaceutically acceptable amount in the range of 0.5-90% w/w;

wherein the combination of B group/complex vitamins comprises at least one of the following B complex vitamins: vitamin B12 (cyanocobalamin), vitamin B1 (thiamine) or its mononitrate salt, vitamin B6 (pyridoxine) or its hydrochloride salt, or a combination of any of these vitamins or their pharmaceutically acceptable salts; and wherein the immediate-release dosage form is selected from the group comprising tablets, pellets, caplets, granules, lozenges, pills, and capsules.

2. The fixed-dose combination drug product according to claim 1, wherein the binder is polyethylene glycol 6000 in an amount ranging from 10-15%.

3. The fixed-dose combination drug product according to claim 1, wherein the fixed-dose combination drug product contains disintegrant is crospovidone in an amount ranging from 2.0-5.0%.

4. The fixed-dose combination drug product according to claim 1, wherein the solubilizer is poloxamer 188 in an amount ranging from 5.0-10.0%.

5. The fixed-dose combination drug product according to claim 1, wherein the lubricant is magnesium stearate in an amount ranging from 0.25-5.0%.

6. The fixed-dose combination drug product according to claim 1, wherein the therapeutically effective quantity of dexketoprofen trometamol contained in this fixed-dose combination drug product is 36.91 mg (equiv to 25 mg).

7. The fixed-dose combination drug product according to claim 1, wherein the therapeutically effective quantities of vitamin B12 (cyanocobalamin), vitamin B1 (thiamine mononitrate), and vitamin B6 (pyridoxine hydrochloride) contained in the fixed-dose combination drug product are 0.50, 100.00, and 50.00 mg, respectively.

8. The fixed-dose combination drug product according to claim 1, wherein the fixed-dose combination drug product is presented as capsules.

9. A method for control and manage pain in a subject suffering from moderate-to severe-intensity acute pain of different etiologies comprising administering a fixed-dose combination drug product of claim 1.

10. The method according to claim 9, wherein the fixed-dose combination drug product aims to treat moderate to severe intensity acute pain of different etiologies resulting from peripheral neuropathies, low back pain, sciatica, neck pain, radiculitis, post-herpetic neuralgia, spondylitis, carpal tunnel syndrome, fibromyalgia, etc., of different etiologies such as inflammatory, drug, diabetic, alcoholic, or nutritional etiology, etc.

11. The method according to claim 9, wherein the fixed-dose combination drug product is an immediate release drug orally administered.

12. The method according to claim 9, wherein the fixed-dose combination drug product contains a combination of dexketoprofen trometamol, cyanocobalamin, thiamine mononitrate, and pyridoxine hydrochloride.

13. The method according to claim 12, wherein the therapeutically effective amount of dexketoprofen trometamol is 12.5 to 75 mg/day and the therapeutically effective amount of vitamin B12 (cyanocobalamin), vitamin B1 (thiamine, mononitrate), and vitamin B6 (pyridoxine, hydrochloride) is 0.50, 100.00, and 50.00 mg, respectively.

14. The method according to claim 13, wherein the therapeutically effective quantity of dexketoprofen trometamol is 36.91 mg (equiv to 25 mg).

* * * * *